US00PP30796P3

(12) United States Plant Patent
Stemkens

(10) Patent No.: US PP30,796 P3
(45) Date of Patent: Aug. 13, 2019

(54) *VERBENA* PLANT NAMED 'VEAZ0052'

(50) Latin Name: *Verbena hybrida*
Varietal Denomination: VEAZ0052

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,005

(22) Filed: Sep. 10, 2018

(65) Prior Publication Data

US 2019/0104667 P1 Apr. 4, 2019

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
See application file for complete search history.

(56) References Cited

PUBLICATIONS

PLUTO Plant Variety Database Apr. 11, 2019.*

* cited by examiner

*Primary Examiner* — Annette H Para
(74) *Attorney, Agent, or Firm* — Dale Skalla

(57) ABSTRACT

A new *Verbena* plant named 'VEAZ0052' particularly distinguished by large sized flowers, shining strawberry colored flowers with a darker-red center, medium green, undivided leaves and a semi-upright and vigorous plant habit.

1 Drawing Sheet

Latin name of the genus and species of the plant claimed: *Verbena hybrida.*

Varietal denomination: 'VEAZ0052'.

BACKGROUND OF THE NEW PLANT

The present invention comprises a new *Verbena*, botanically known as *Verbena hybrida*, and hereinafter referred to by the variety name 'VEAZ0052'.

'VEAZ0052' is a product of a planned breeding program. The new cultivar has large sized flowers, shining strawberry colored flowers with a darker-red center, medium green, undivided leaves and a semi-upright and vigorous plant habit.

'VEAZ0052' originated from a cross made in July 2011 in a greenhouse in Enkhuizen, The Netherlands. The female parent plant was an unpatented propriety plant named 'L0638-2' having a bright rose color and even bigger flowers. The male parent was an unpatented propriety plant named 'N1278-4' having a deep scarlet color and a very compact plant habit 'VEAZ0052' was selected as one flowering cutting of the stated plant in July 2012 and immediately reproduced.

The first act of asexual reproduction of 'VEAZ0052' was accomplished when vegetative cuttings were propagated in July 2012 in a greenhouse in Enkhuizen, The Netherlands.

BRIEF SUMMARY OF INVENTION

Horticultural examination of plants grown from cuttings of the plant initiated in the fall of 2011, and continuing thereafter, has demonstrated that the combination of characteristics as herein disclosed for 'VEAZ0052' are firmly fixed and are retained through successive generations of asexual reproduction.

'VEAZ0052' has not been observed under all possible environmental conditions. The phenotype may vary significantly with variations in environment such as temperature, light intensity, and day length.

A Plant Breeder's Right for this cultivar was applied for in the European Union on Oct. 2, 2017, No. 2017/2457. 'VEAZ0052' has not been made publicly available prior to the effective filing date of this application, notwithstanding any disclosure that may have been made less than one year prior to the effective filing date of this application by the inventor or another who obtained 'VEAZ0052' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0052' with colors being as true as possible with an illustration of this type.

Figure 1:
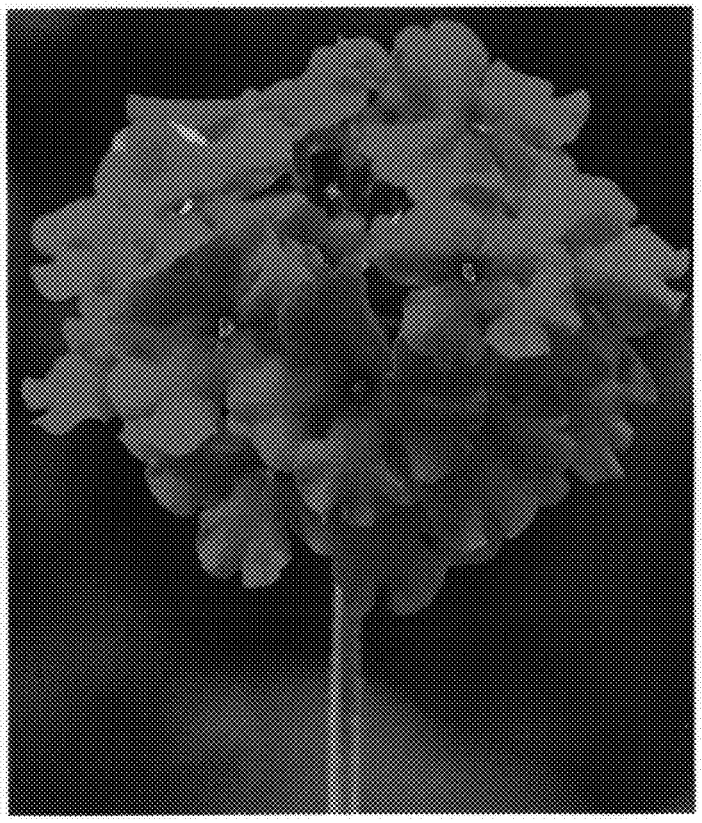

FIG. 1 shows a close view of an inflorescence of the new plant, and in

Figure 2:
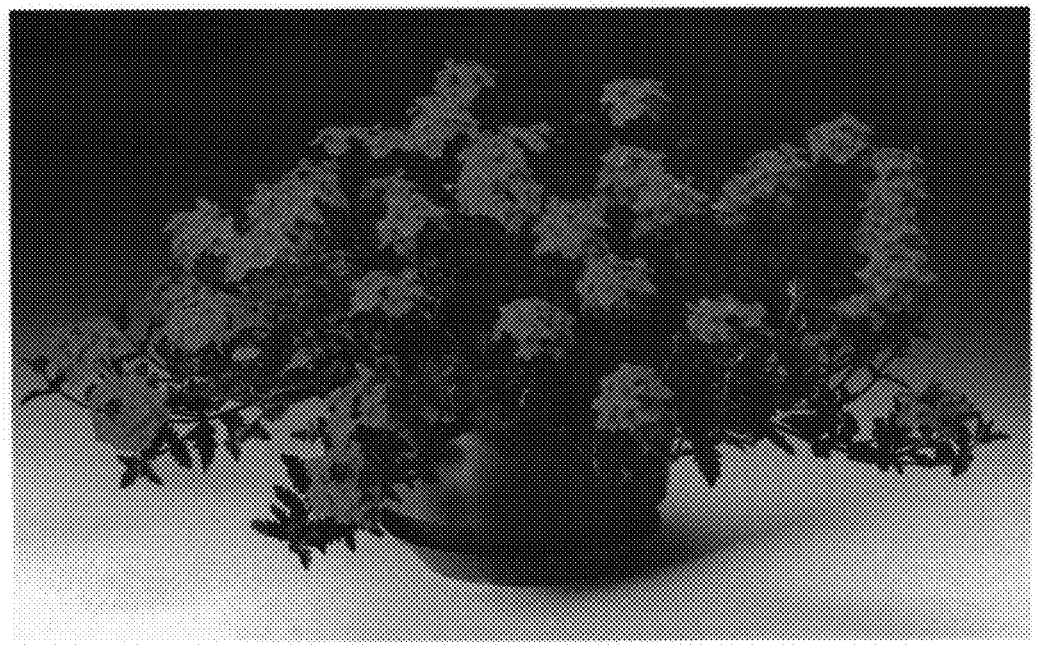

FIG. 2 a whole flowering plant.

The aforementioned photographs were taken in July 2018 in Andijk, The Netherlands. The plants were about 12 weeks old and were grown in 12 cm pots.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0052' AND A MOST SIMILAR VARIETY

| | 'VEAZ0052' | 'Arbena' (U.S. Pat. No. PP15,760) |
|---|---|---|
| Flower color: | Darker strawberry | Lighter strawberry and fading |
| Flower, size: | larger | Smaller |
| Leaf, size: | Large | Small |

Plant:

*Form, growth and habit.*—Herbaceous, semi-trailing and vigorous.

*Plant height.*—22.0 cm.

*Plant height (inflorescence included).*—28.0 cm.

*Plant width.*—48.0 cm.

Roots:

*Number of days to initiate and produce roots.*—11-14 days at about 21 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 144B.

*Immature, leaf color, lower surface.*—RHS 138C.

*Mature, leaf color, upper surface.*—RHS 144A.

*Mature, leaf color, lower surface.*—RHS 137D.

*Length.*—Approximately 3.5 cm.

*Width.*—3-3.3 cm.

*Shape.*—Hastate.

*Base shape.*—Obtuse.

*Apex shape.*—Obtuse.

*Margin.*—Lobed.

*Texture, upper surface.*—Pubescent.

*Lower surface.*—Pubescent.

*Color of veins, upper surface.*—RHS 145B.

*Color of veins, lower surface.*—RHS 145A.

*Pattern of veining.*—Pinnate.

*Petiole color.*—RHS 145B.

*Petiole length.*—0.6 cm.

*Petiole width.*—0.4 cm.

*Texture.*—Hirsute.

Stem:

*Branching characteristics.*—Side branches develop potentially at each node.

*Quantity of main branches per plant.*—12-15.

*Color of stem.*—RHS 144A.

*Stem length.*—21.0-30.0 cm.

*Stem width.*—0.25 cm.

*Length of internodes.*—2 to 3.2 cm.

*Texture.*—Hirsute.

*Color of peduncle.*—RHS 137C.

*Length of peduncle.*—2.8 to 4.2 cm.

*Peduncle diameter.*—0.2 cm.

*Texture.*—Glandular hairs.

Inflorescence:

*Type.*—Umbel-like, but actually a spike, umbrella-shaped.

*Blooming habit.*—Flowers develop continuously during the summer months.

*Lastingness of individual blooms on the plant.*—About 3-4 days in the greenhouse.

*Fragrance.*—None.

*Number of inflorescences per plant.*—46 at various stages at development.

*Horizontal diameter of inflorescence.*—6.2-6.7 cm.

*Depth of inflorescence.*—3.9 cm.

*Number of florets and buds per inflorescence.*—Approximately 38-40.

Bud:

*Color.*—RHS N155B.

*Length.*—0.3 cm.

*Width.*—0.25 cm.

*Shape.*—Tubular with bulbous apex.

Floret:

*Form.*—Sessile; salver-shaped, composed of 5 partly fused petals with a base of a narrow tube.

*Immature color, upper surface.*—RHS 47A with to the center RHS 48A.

*Immature color, lower surface.*—RHS 47C.

*Mature color, upper surface.*—RHS 48B with to the center RHS 46A.

*Mature color, lower surface.*—RHS 47C.

*Floret diameter.*—5.8 cm.

*Floret length (depth).*—4.0 cm.

*Petal length.*—1.7 cm.

*Petal width.*—1.4 cm.

*Shape.*—Obcordate.

*Apex shape.*—Emarginate.

*Margin.*—Entire.

*Petal texture, upper surface.*—Papillose.

*Petal texture, lower surface.*—Papillose, pubescent.

*Corolla tube length.*—2.6 cm.

*Corolla tube width.*—0.2 cm.

*Corolla tube color inside.*—RHS 47C.

*Tube color outside.*—RHS 47B.

*Corolla texture, inside.*—Pubescent.

*Corolla texture, outside.*—Canescent.

*Throat hair color.*—RHS 155C but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 144B.

*Length of sepals.*—1.3 cm.

*Width of sepals.*—0.2 cm.

*Sepal shape.*—Fused, linear.

*Apex shape.*—Acute.

*Margins.*—Entire.

*Texture.*—Densely covered with very short glandular hair.

Reproductive organs:

Gynoecium:

*Pistil.*—1.

*Pistil length.*—1.6 cm.

*Style color.*—RHS 144B.

*Style length.*—1.6 cm.

*Stigma color.*—RHS 144A.

*Ovary color.*—RHS 144B.

*Ovary length.*—0.2 cm.

*Ovary width.*—0.1 cm.

Androecium:

*Stamens.*—Anthers and filaments fused to upper half of corolla tube; four anthers with two pollen sacs per anther.

*Color of filaments.*—RHS 151D.

*Filament length.*—0.2 cm.

*Anther color.*—RHS 151C.

*Anther length.*—0.1 cm.

*Pollen amount.*—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0052' substantially as illustrated and described herein.

* * * * *